(12) United States Patent
Hancock

(10) Patent No.: US 7,229,419 B2
(45) Date of Patent: Jun. 12, 2007

(54) SINGLE-HANDED BIOPSY SYSTEM

(75) Inventor: John Phillip Hancock, Fishers, IN (US)

(73) Assignee: Promex/U.S. Biosy LLC, Franklin, IN (US)

( * ) Notice: Subject to any disclaimer, the term of this patent is extended or adjusted under 35 U.S.C. 154(b) by 267 days.

(21) Appl. No.: 10/776,750

(22) Filed: Feb. 11, 2004

(65) Prior Publication Data

US 2004/0158172 A1 Aug. 12, 2004

Related U.S. Application Data

(60) Provisional application No. 60/447,235, filed on Feb. 12, 2003, provisional application No. 60/446,745, filed on Feb. 11, 2003.

(51) Int. Cl.
*A61B 10/00* (2006.01)
(52) U.S. Cl. ............................... 600/567
(58) Field of Classification Search ........ 600/564–567; 606/167, 170
See application file for complete search history.

(56) References Cited

U.S. PATENT DOCUMENTS

| | | | | |
|---|---|---|---|---|
| 4,699,154 A | 10/1987 | Lindgren | ................ | 128/754 |
| 4,944,308 A | 7/1990 | Akerfeldt | ................ | 128/751 |
| 4,953,558 A | 9/1990 | Akerfeldt | ................ | 128/751 |
| 4,958,625 A | 9/1990 | Bates | ................ | 128/754 |
| 5,025,797 A | 6/1991 | Baran | ................ | 128/754 |
| 5,121,751 A | 6/1992 | Panalletta | ................ | 128/754 |
| 5,125,413 A | 6/1992 | Baran | ................ | 128/754 |
| 5,284,156 A | 2/1994 | Schramm | ................ | 128/754 |
| 5,368,045 A | 11/1994 | Clement | ................ | 128/754 |
| 5,476,101 A | 12/1995 | Schramm | ................ | 128/754 |
| 5,507,298 A | 4/1996 | Schramm | ................ | 128/754 |
| 5,538,010 A | 7/1996 | Darr | ................ | 128/754 |
| 5,546,957 A | 8/1996 | Heske | ................ | 128/754 |
| 5,752,923 A * | 5/1998 | Terwilliger | ................ | 600/562 |
| 6,126,617 A * | 10/2000 | Weilandt et al. | ................ | 600/567 |
| 6,221,030 B1 | 4/2001 | Avaltroni | ................ | 600/567 |
| 2002/0120212 A1* | 8/2002 | Ritchart et al. | ................ | 600/567 |
| 2003/0163152 A1* | 8/2003 | Weilandt et al. | ................ | 606/167 |
| 2004/0097830 A1 | 5/2004 | Cooke | | |

* cited by examiner

*Primary Examiner*—Max F. Hindenburg
*Assistant Examiner*—Michael Apanius
(74) *Attorney, Agent, or Firm*—Maginot, Moore & Beck

(57) ABSTRACT

An automatic tissue sampling apparatus for use with a biopsy needle set having an inner needle and an outer cannula is provided. The apparatus includes a slidably disposed, spring-biased carrier for each of the inner needle and cannula. A cocking mechanism is operable to sequentially move the first carrier to its cocked position and the second carrier to its cocked position. The cocking mechanism includes a manually operated cocking lever positioned outside the housing for single handed manipulation while holding the housing. A force transmission mechanism is operably coupled between the cocking lever and the carriers and configured so that the force required to manually depress the cocking lever to force the springs to the cocked positions does not increase as the springs are compressed.

13 Claims, 22 Drawing Sheets

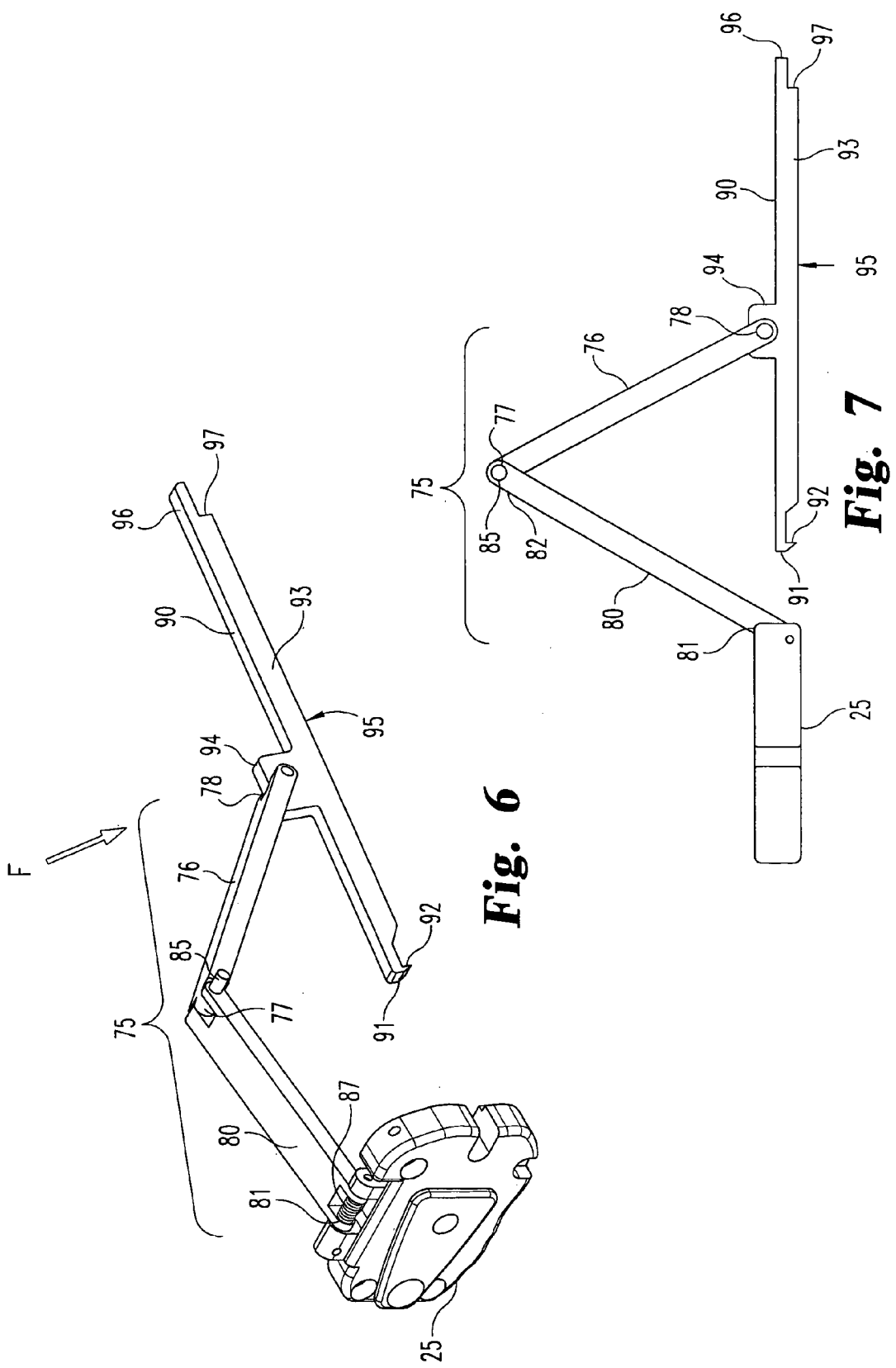

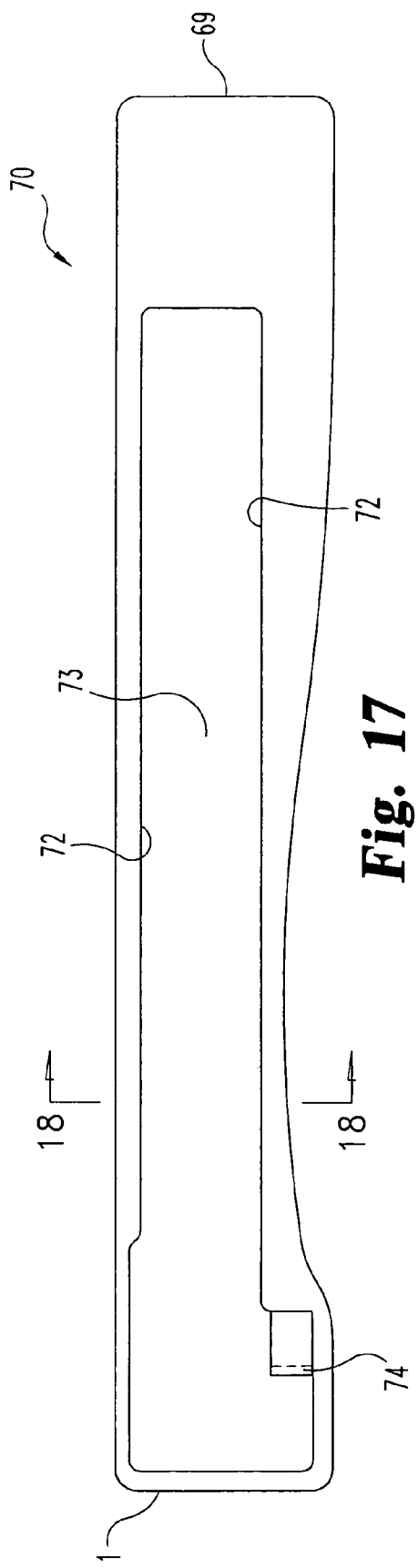
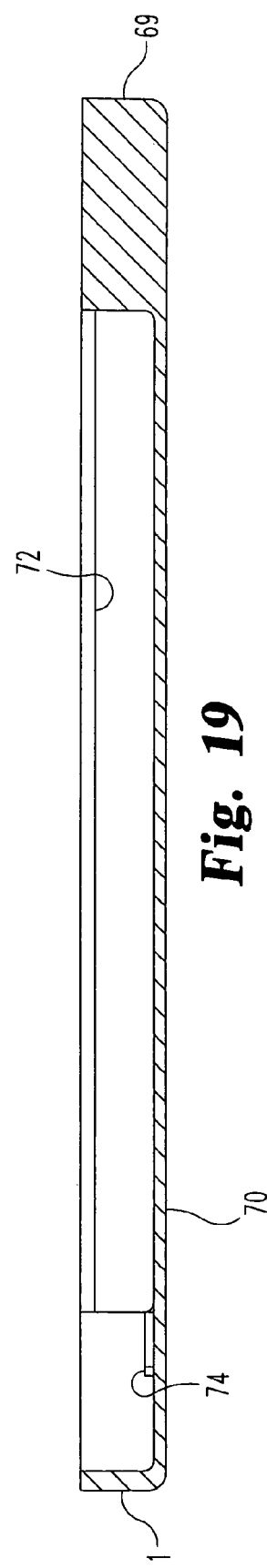
Fig. 17
Fig. 18
Fig. 19

SINGLE-HANDED BIOPSY SYSTEM

This application claims priority to Provisional application 60/446,745 filed Feb. 11, 2003 entitled BIOPSY DEVICE and to Provisional application 60/447,235 filed Feb. 12, 2003 entitled BIOPSY DEVICE.

FIELD OF THE INVENTION

The present invention generally relates to the field of tissue sampling and harvesting. The invention more specifically relates to biopsy guns and needles.

BACKGROUND OF THE INVENTION

Examples of typical double action biopsy guns are described in U.S. Pat. Nos. 4,699,154, 4,944,308, 5,284,156 and 6,221,030. Prior art biopsy guns are well know and widely used, but they suffer from certain significant drawbacks. For example, know prior art double action biopsy guns require the use of two hands. This is unfortunate because the tissue sampling is typically performed under visualization, such as ultra sound. It would be convenient to have a free hand to operate the visualization equipment. Many devices also make a compromise between sample quality and cocking force. To achieve significant needle velocity, prior art devices have required significant cocking force. To reduce cocking force has meant poorer sample quality.

Therefore, a need remains for double action biopsy guns that can be cocked and fired using a single hand yet which reliably provide high quality tissue samples.

BRIEF DESCRIPTIONS OF DRAWINGS

FIG. 6 is a side perspective view of a cocking slider and a force transmission mechanism engaged to the forward end of a device according to one embodiment of this invention.

FIG. 7 is a side elevational view of the components shown in FIG. 6.

FIG. 17 is a elevational view of the internal surface of the cocking lever according to one embodiment of this invention.

FIG. 18 is a cross sectional view taken along lines 18—18 of the cocking lever shown in FIG. 17.

FIG. 19 is a longitudinal sectional view of the cocking lever shown in FIG. 17.

Figure 1:
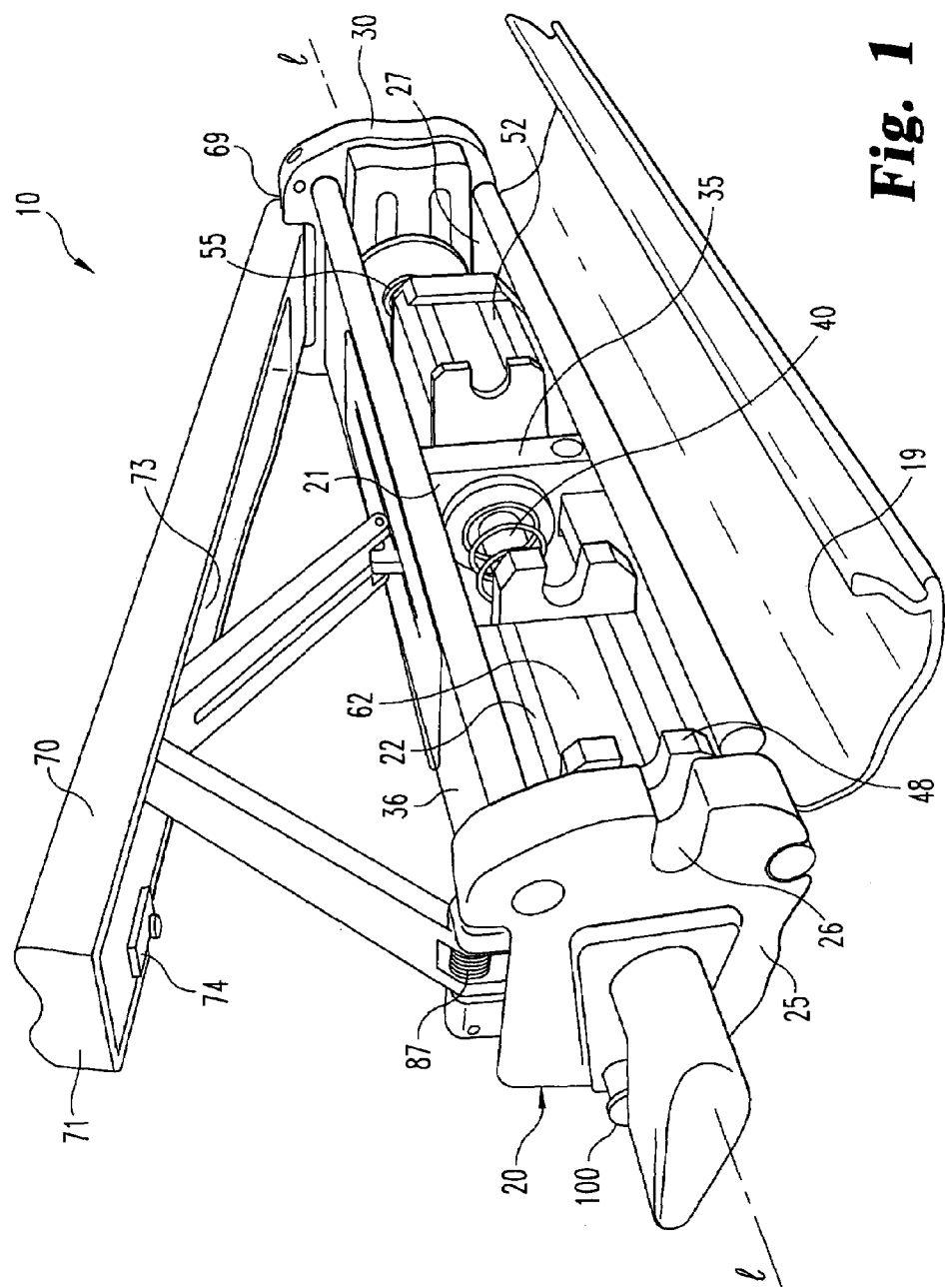
FIG. 1 is a side perspective view of a biopsy gun according to one embodiment of this invention.

Although the drawings represent embodiments of the present invention, the drawings are not necessarily to scale and certain features may be exaggerated in order to better illustrate and explain the present invention. The exemplification set out herein illustrates certain embodiments of the invention, in one, or more forms, and such exemplifications are not to be construed as limiting the scope of the invention in any manner.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The present invention provides devices for automated tissue sampling. The devices of this invention can be operated with a single hand without compromising sample quality or efficiency.

FIG. 1 shows a biopsy gun 10 according to one embodiment of this invention. The biopsy gun 10 can be used with coaxial core biopsy needle sets, which are commercially available from US Biopsy, 3049 Hudson Street, Franklin, Ind. 46131 (800-755-1671). The biopsy needle sets include an inner needle or stylet having a first hub disposed at one end and a cutting point disposed on an opposite end with a tissue holding notch positioned between the cutting point and the first hub. The inner needle is disposed within an outer cannula, which has a second hub at one end and a cutting point disposed at the opposite end.

Biopsy device 10 includes a housing 20 defining an interior cavity 21 and a cover 19. The interior cavity 21 includes a forward portion 22 adjacent a forward end of the housing 20, which defines an opening 26 in communication with the interior cavity 21 for passage of the needle set. The interior cavity 21 also includes a rearward portion 27 adjacent a rearward end 30 with a transverse wall 35 disposed between the forward region 22 and the rearward region 27. A rotatable center shaft 40 is disposed within the housing 20 along a longitudinal axis l of the housing 20.

Figure 2:
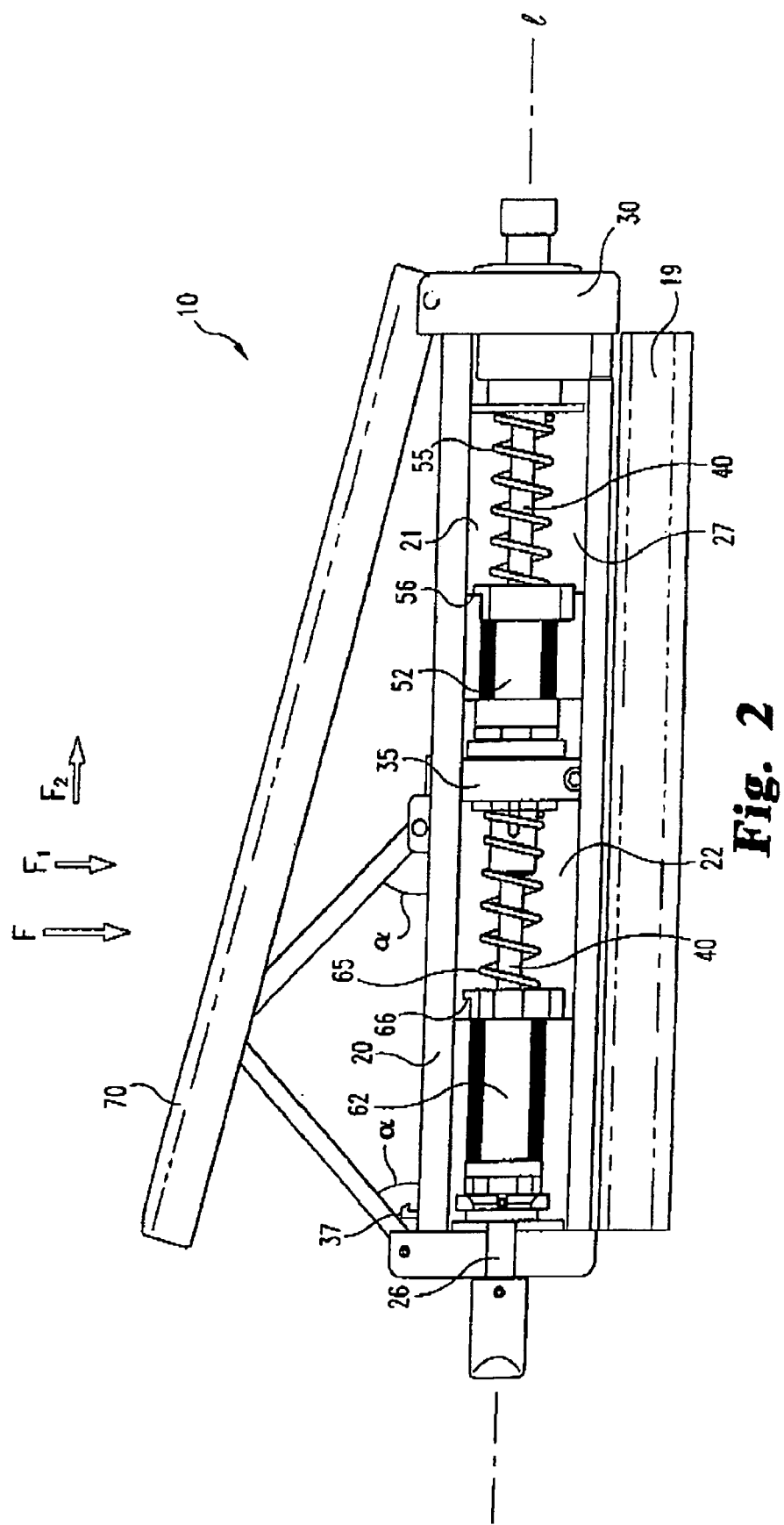
FIG. 2 is a side elevational view of the gun of FIG. 1 shown in the resting position.
Figure 3:
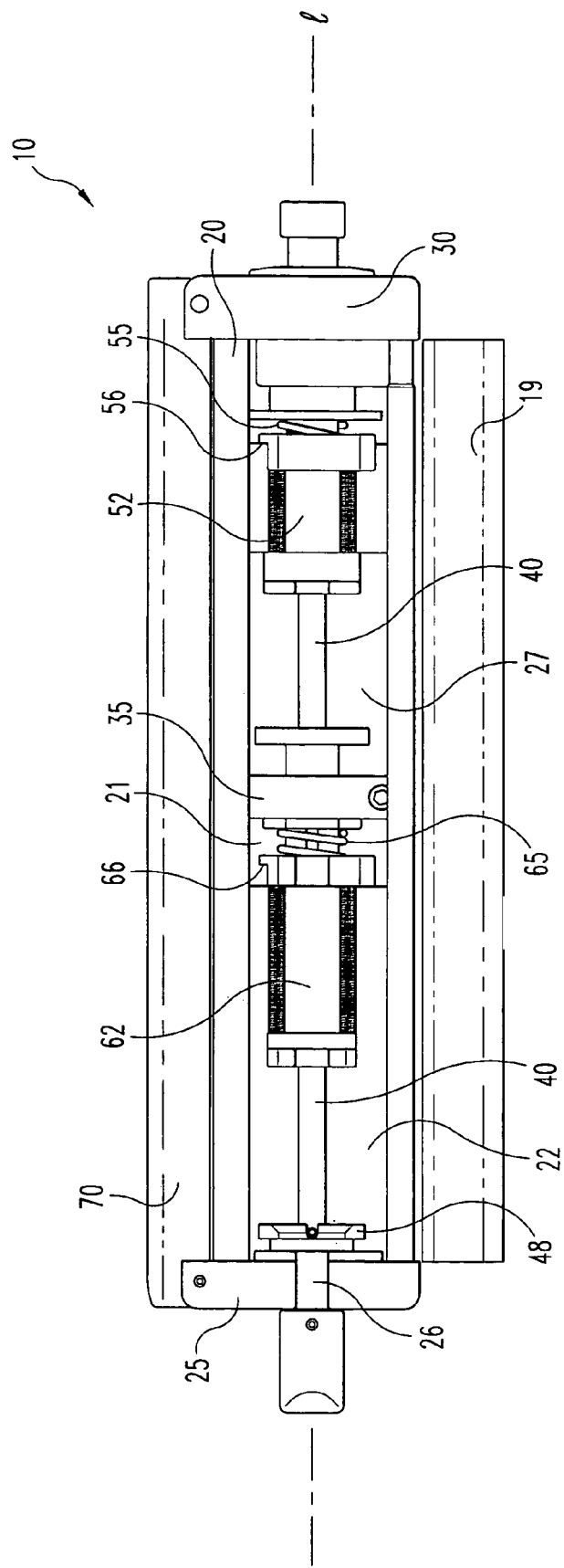
FIG. 3 is a side elevational view of the gun of FIG. 1 shown in the cocked position.
Figure 4:
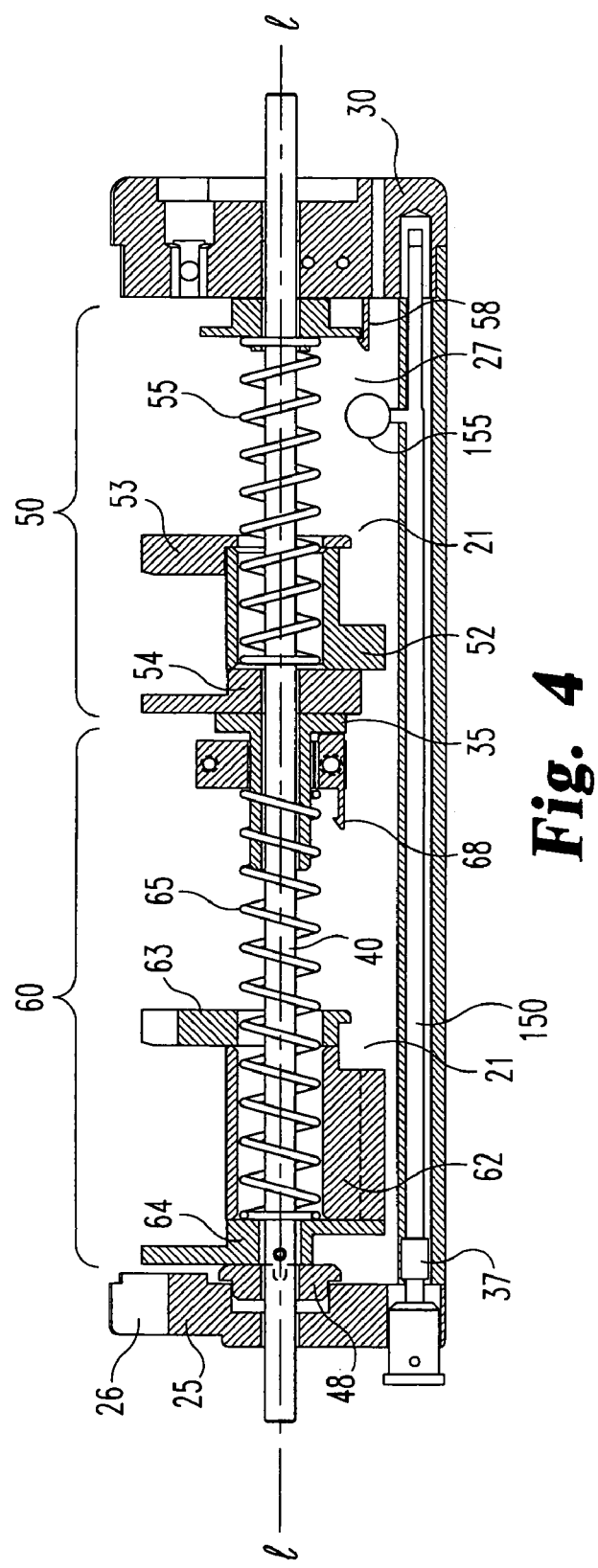
FIG. 4 is a longitundinal section of the view shown in FIG. 2.

Referring also now to FIGS. 2–4, the device 10 includes a rearward carrier assembly 50 configured to receive, support and carry one of the needle hubs. In one embodiment the rearward assembly is configured to carry an inner stylet hub. The rearward carrier assembly 50 includes a rearward carrier 52, a rearward drive mechanism 55 and a rearward retaining member 58. The rearward carrier 52 has a hub support portion 54 and a rearward drive portion 53 mounted on the center shaft 40 in the rearward portion 27. The rearward carrier 52 is movable on the center shaft 40 along a path substantially parallel to the longitudinal axis l of the housing between a first resting position as shown in FIG. 2 and a first cocked position as shown in FIG. 3.

The rearward drive mechanism 55 is disposed within the interior cavity in operable engagement with the rearward carrier 52. The rearward drive mechanism 55 is movable between a cocked position in which the drive mechanism stores potential energy and a firing position in which the mechanism releases the potential energy to drive the rearward carrier 52 forward toward the forward end 25 of the housing 20. In one embodiment, the rearward drive mechanism includes a rear spring member 55. The rear spring member 55 is positioned within the rearward region 27 of the housing 20 and biases the rearward carrier 52 forwardly toward the first resting position. The rear spring member 55 is compressible to the cocked position.

The rearward retaining member 58 can be an L-shaped hook member biased upwardly with a leaf or other spring. The retaining member 58 is configured to releasably retain the rearward carrier 52 in the cocked position. The rearward retaining member 58 is releasable in response to a trigger 100 operatively engaged to the rearward retaining member 58.

The device 20 also includes a forward carrier assembly 60 configured to receive, support and carry the other one of the needle hubs. In one embodiment, the forward carrier is configured to carry an outer cannula hub. The forward carrier assembly 60 includes a forward carrier 62, a forward drive mechanism 65 and a forward retaining member 68. The forward carrier 62 has a hub support portion 64 and a forward drive portion 63 mounted on the center shaft 40 in the forward portion 22. The forward carrier 62 is movable on the center shaft 40 along a path substantially parallel to the longitudinal axis l of the housing between a second resting position as shown in FIG. 2 and a second cocked position as shown in FIG. 3.

The forward drive mechanism is disposed within the interior cavity 21 in operable engagement with the forward carrier 62. The forward drive mechanism is movable between a cocked position in which the drive mechanism stores potential energy and a firing position in which the mechanism releases the potential energy to drive the forward carrier 62 forward toward the forward end 25 of the housing 20. In some embodiments, the forward drive mechanism includes a front spring member 65. The front spring member 65 is positioned within the forward region 22 of the housing 20 and biases the forward carrier 62 forwardly toward the second resting position. The front spring member 65 is compressible to the cocked position.

The forward retaining member 68 is configured to releasably retain the forward carrier 62 in the second cocked position. The forward retaining member 68 is releasable in response to the rearward carrier 52 moving from the first cocked position to the first resting position.

The hub support portions 54, 64 of both of the carriers 52, 62 can be equipped with desirable features, such as those that will support and maintain the hubs in a desired relationship by preventing rotation, for example. Other such suitable features are contemplated by this invention.

The device 10 includes a cocking mechanism operable to sequentially move the driving mechanisms to the corresponding cocked positions. In some embodiments, the cocking mechanism is a two stage cocking assembly that moves one of the carriers to the corresponding cocked position with a first actuation of the cocking assembly and then moves the other of the carriers to the corresponding cocked position with a second actuation of the cocking assembly.

The cocking mechanism includes a manually operated cocking lever 70 positioned outside the housing 20 for single handed manipulation while holding the housing. Referring again to FIGS. 1 and 2, the cocking lever 70 is pivotally mounted to the housing 20 at a point 69 and can be manually depressed against the housing 20. The cocking lever 70 is disposed externally on a lever wall 36 of the housing 20. In one specific embodiment, the lever wall 36 is disposed between the forward end 25 and the rearward end 30 of the housing 20 and the cocking lever 70 is laterally supported from the lever wall 36.

The cocking mechanism includes a force transmission mechanism operably coupled between the cocking lever 70 and each of the carriers 52, 62. Due to the force transmission mechanism of this invention, the force required to manually depress the cocking lever 70 to compress each of the forward and rear springs 65, 55 does not increase as the spring is compressed. The lever has a declining operator force requirement that compensates for the increasing force required to further compress each spring. The lateral position of the lever 70 and the declining operating force allow single-handed use of the device without compromising spring force and sample quality.

Referring now to FIGS. 6 and 7, in some embodiments, the cocking assembly also includes a cocking slider 90 having an elongated bar portion 93. The slider 90 is movable along a path in response to actuation of the cocking lever by action of the force transmission mechanism.

The cocking slider 90 includes a forward engagement member 92 at a forward end 91 releasably engageable to an engagement portion 66 (FIG. 2) on the forward carrier 62. A rearward engagement member 97 is also provided at a rearward end 96 of the slider 90, which is releasably engageable to an engagement portion 56 (FIG. 2) on the rearward carrier 52. In a specific embodiment, the forward engagement member 92 is shaped as a hook configured to drag the forward carrier 62 back to the cocked position. The rearward engagement member 97 can be shaped as a notch to serve as a pusher element as shown in FIG. 6 to push the rearward carrier 52 back to the cocked position. In other specific embodiments, the cocking slider 90 includes a beam-cocking slider connector 94 forward of the center 95 of the elongated bar 93.

As shown in FIGS. 8–13, the cocking slider 90 has a length sufficient to span a distance between the forward carrier 62 and the rearward carrier 52. The cocking slider 90 is slidably disposed within the housing 20 so that when the cocking slider 90 slides in a rearward direction R away from the forward end 25 of the housing 20 and an engagement portion 92, 97 applies a force against one of the carriers 52, 62, the carrier is moved to its cocked position.

Referring again also to FIGS. 6 and 7, the force transmission mechanism 75 is engaged between the cocking lever and the cocking slider. The mechanism 75 translates the pivoting movement of the cocking lever 70 to the sliding movement of the cocking slider 90 in the rearward direction R against the carriers 52, 62. The force transmission mechanism includes an elongated rearward beam 76 pivotally connected at a first end 78 to the slider 90 and slidably supported at an opposite end 77 by the cocking lever 70. In one specific embodiment, the beam 76 is connected to the beam-slide connector 94 of the slider 90. A forward beam 80 is pivotally connected at one end 81 to the housing 20. In one specific embodiment, the forward beam is engaged to the forward end 25 of the housing 20. A beam bearing 85 is slidably supported by the cocking lever 70 and pivotally connects the ends 77, 82 of the beams 76, 80.

The force transmission mechanism 75 also includes a biasing element 87 at the one end 81 of the forward beam 80. The biasing element 87 biases the beam away from the housing 20, which in turn pivots the cocking lever 70 away from the housing 20 when the cocking lever 70 is not latched.

The cocking slider 90 is disposed between the cocking beams 76, 80 and the carriers 52, 62 to transmit force from the lever 70 to the beams 76, 80 to the carriers 52, 62 to move the carriers 52, 62 from the corresponding resting position to the corresponding cocked position. Referring again to FIG. 2, each of the cocking beams 76, 80 form an angle $\alpha$ with the lever wall 36 of the housing 20. The beam bearing 85 is movable against the cocking lever 70 between a lever open position with the cocking beams 76, 80 in a retracted position (FIG. 2) and a lever closed position with the cocking beams 76, 80 in an extended position (FIG. 3). The angle $\alpha$ is smaller when the cocking beams 76, 80 are in the extended position relative to when the cocking beams 76, 80 are in the retracted position. In a specific embodiment, angle $\alpha$ is approximately 45° in the retracted position. Therefore, applying a force F on the lever transmits roughly half of the force in the direction of arrow $F_1$ and half of the force in the direction of arrow $F_2$. As angle $\alpha$ decreases, a mechanical advantage is achieved as more of the force F is applied in the direction of arrow $F_2$, which makes closing the lever easier. However, as the spring 55, 65 compresses, it requires more force to continue compression. The declining force requirement on the lever 70 makes the increased force requirement of the spring transparent to the user.

Figure 8:
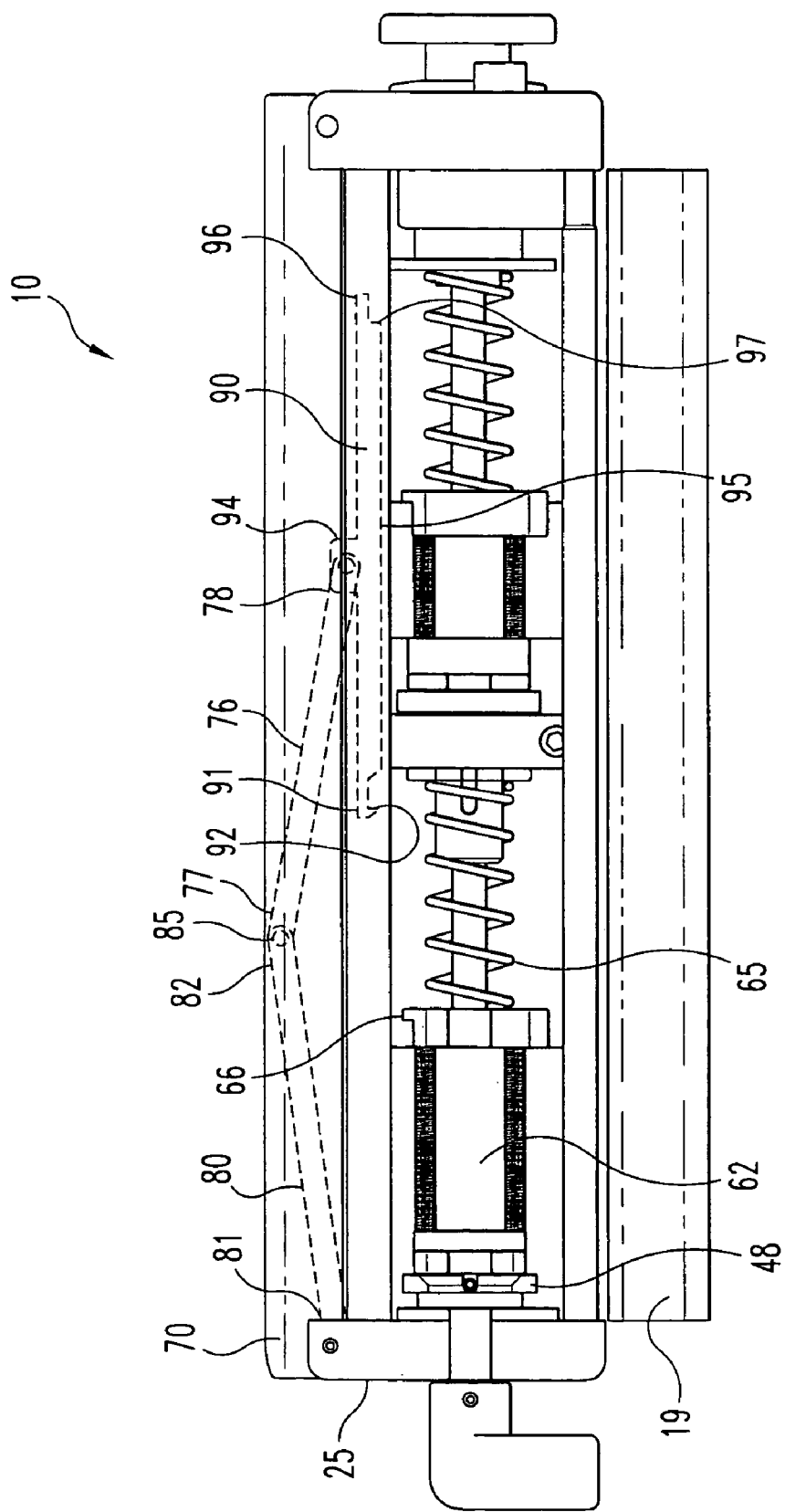
FIG. 8–13 are partial side sectional views of a device shown moving through the cocking and firing sequence according to one embodiment of this invention.
Figure 9:
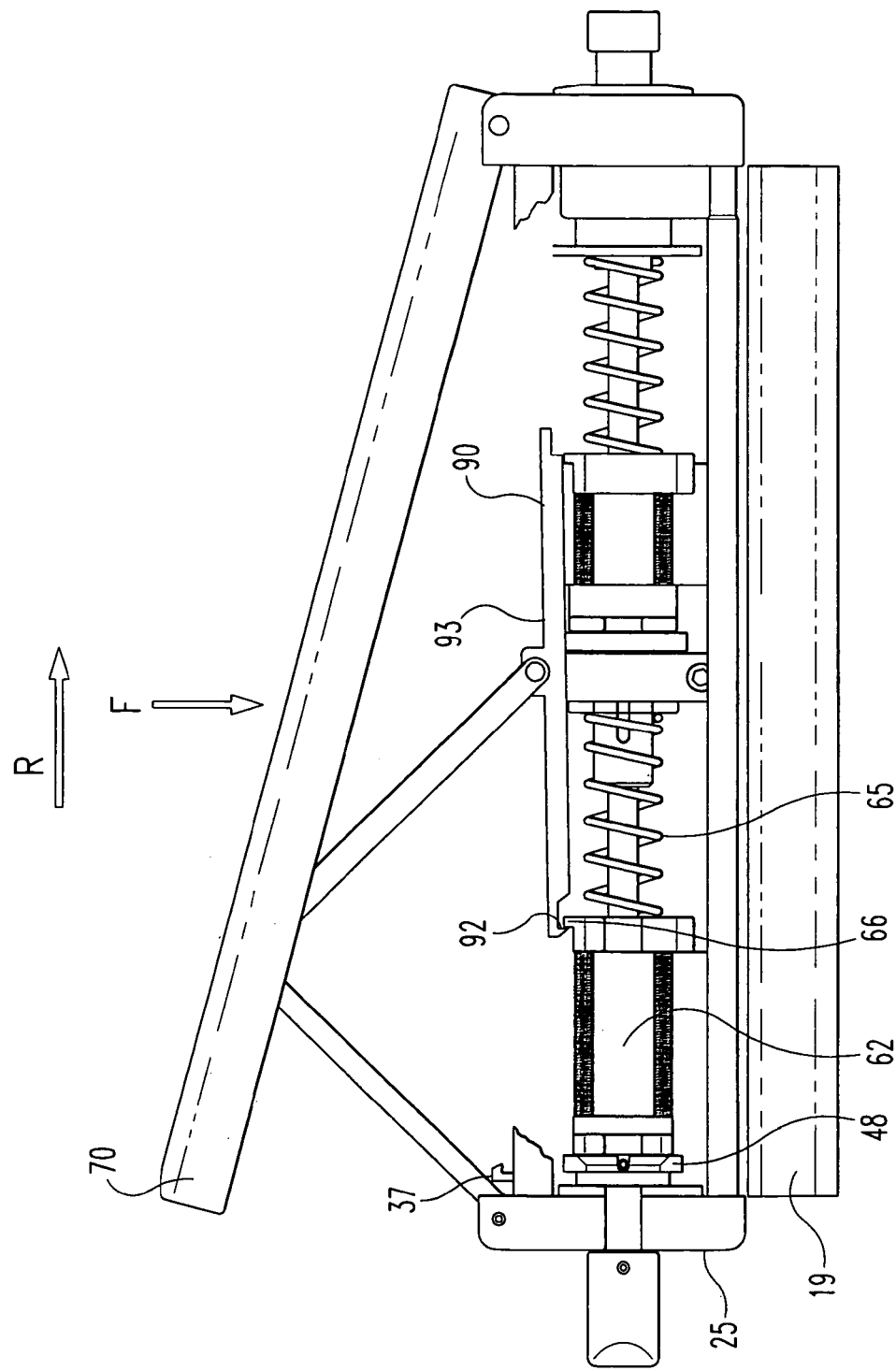
Figure 10:
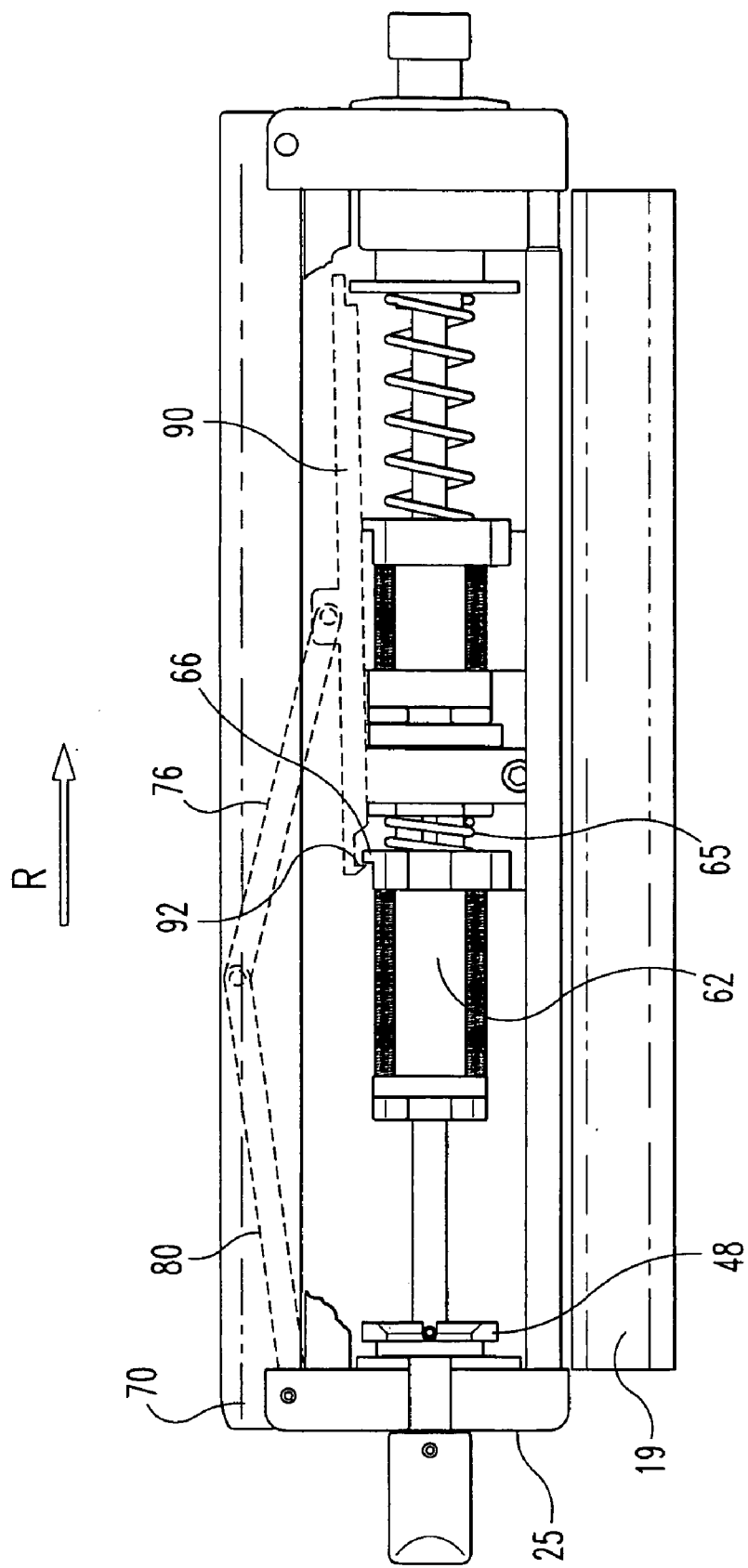
Figure 11:
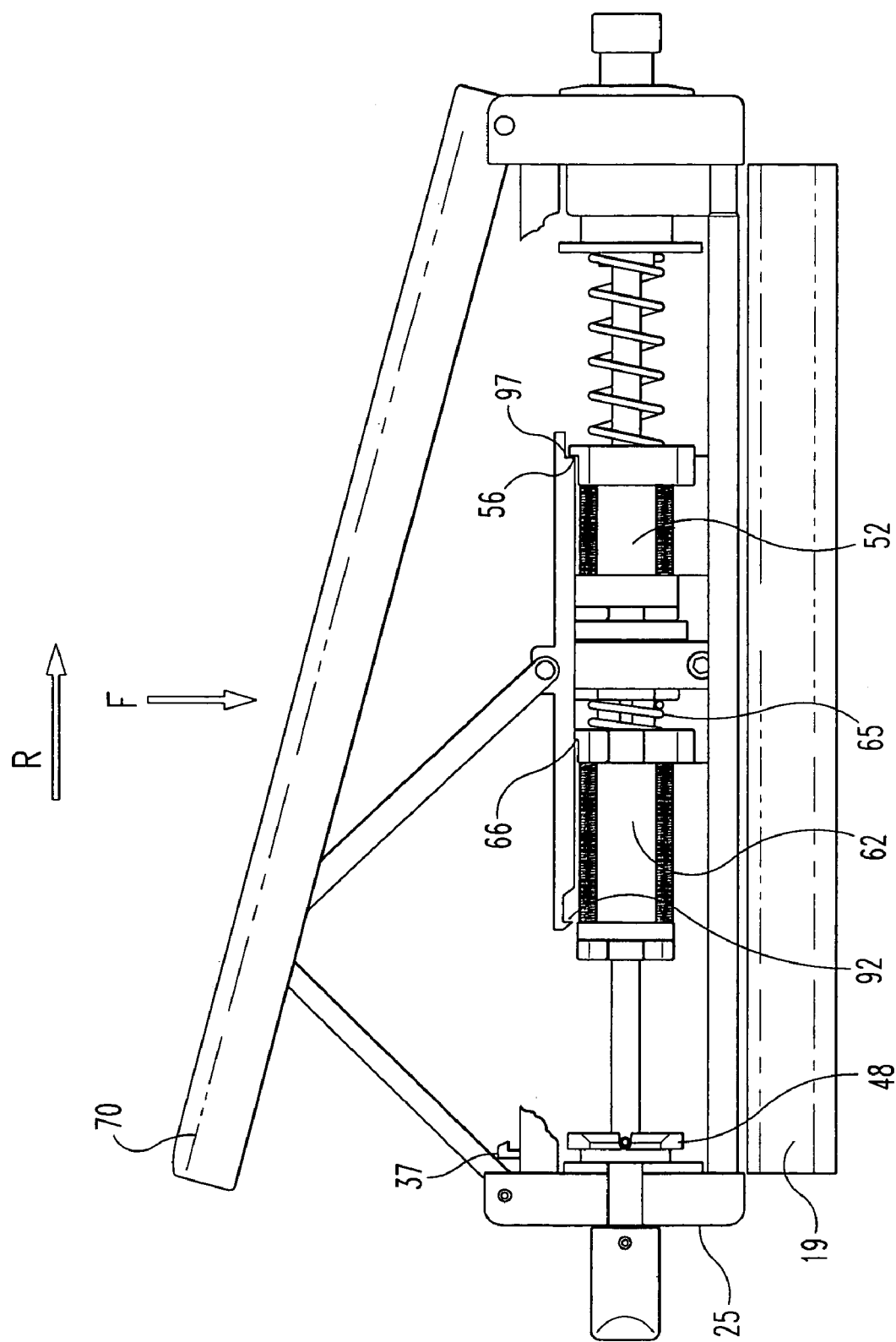

The operation of one embodiment of the force transmission mechanism 75 and the cocking slider 90 is shown in FIGS. 8–13. In FIG. 8, the device 10 is shown in a resting state with the safety off and the cover 19 open. The safety is then turned to the safety-on position, which prevents actuation of the trigger. In the safety-on positions the cocking lever 70 is unlatched and opens as shown in FIG. 9. As the cocking lever 70 swings open, the cocking slider 90 moves forward so that the forward engagement member 92 is aligned with the forward carrier engagement portion. Upon actuation of the cocking lever 70, force F is applied to the bar 93 at the beam-slider connector 94. Because the connector 94 is forward of the center 95 of the slider bar 93 and the rearward end 96 of the slider 90 rests on the engagement portion 56 of the rearward carrier 52, the forward end 91 of the slider tips toward the forward carrier 62 to engage the forward engagement member 92 with the forward carrier 62. As the cocking lever is closed, the slider 90 is forced backward and drags the forward carrier to the cocked position against the bias of the spring 65 as shown in FIG. 10.

When the force F is released, the cocking lever 70 swings open again and the slider 90 slides to the forward position (FIG. 11) with the rearward engagement member 97 aligned with the rearward carrier engagement portion 56. This time, when the force F is applied, the slider 90 is prevented from tilting in the forward direction by the presence of the forward carrier 62, and the slider tilts towards the rearward carrier 52, engages and pushes the rearward carrier 52 back to the cocked position.

Figure 12:
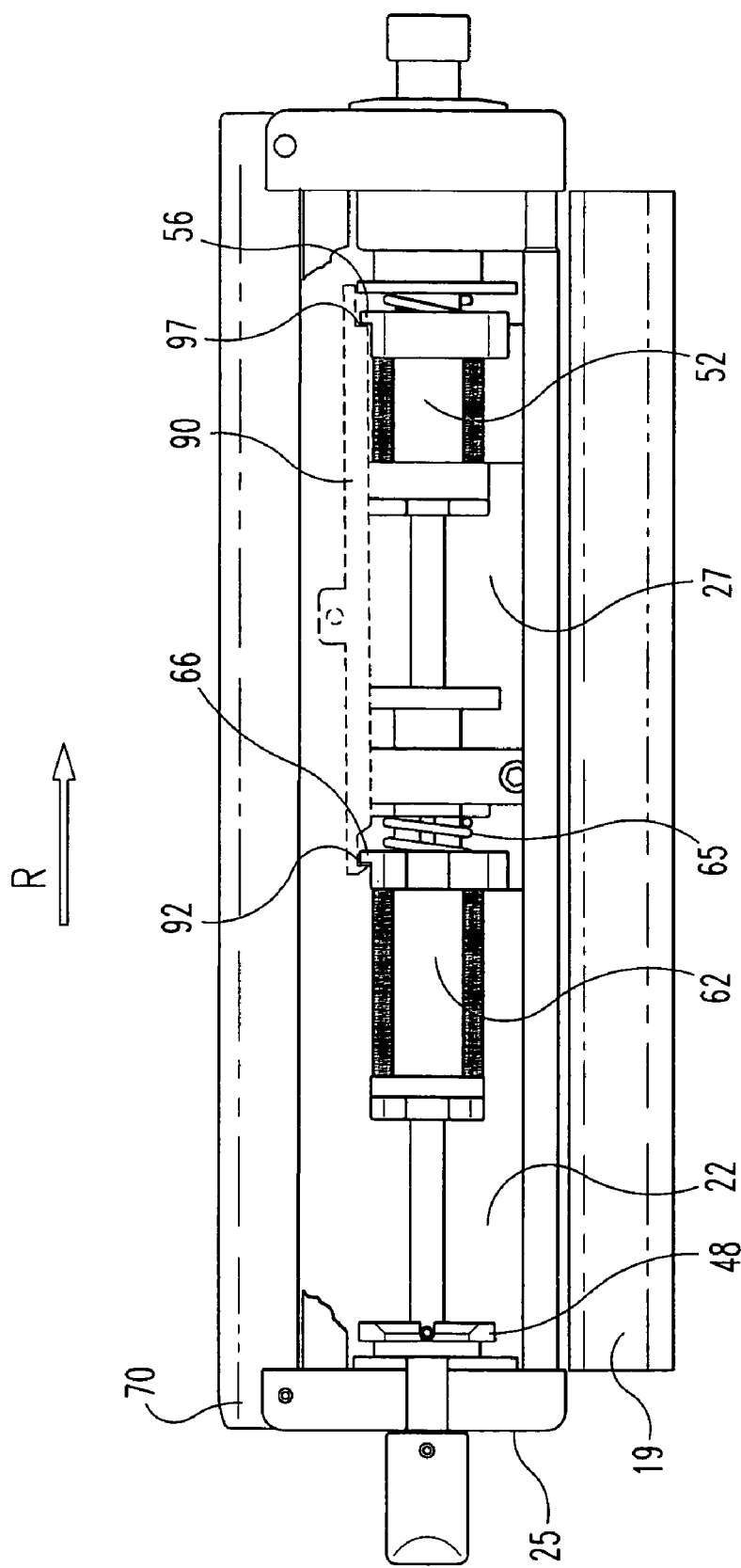

The fully cocked configuration is shown in FIG. 12. At this step, the gun cannot fire because the safety mechanism prevents the actuation of the trigger. In addition, the slider 90 may still be engaged to one or both of the cannula carriers 52, 62.

Figure 14:
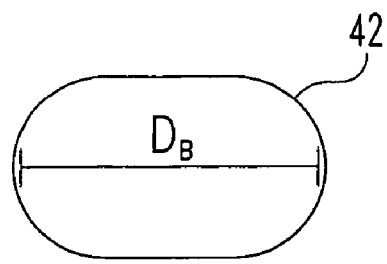
FIG. 14 shows the shape of the rear cam plate.
Figure 15:
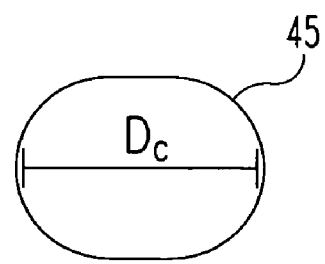
FIG. 15 shows the shape of the center cam plate.
Figure 16:
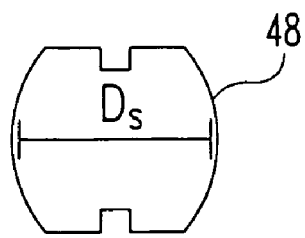
FIG. 16 is an elevational view of the front safety cam.

Rotating the safety allows the trigger to be actuated. In some embodiments, rotating one of the safety knobs rotates a cam that pushes the slider 90 up and away from the carriers 52, 62. In the embodiment shown in FIG. 13, a back elliptical plate 42 (FIG. 14) and a center elliptical plate 45 (FIG. 15) rotate with the rotatable shaft 40. Both the back and center elliptical plates 42, 45 have a major dimension $D_B$, $D_C$ sufficient to push the slider 90 from the position shown in FIG. 12 to the position shown in FIG. 13.

Figure 13:
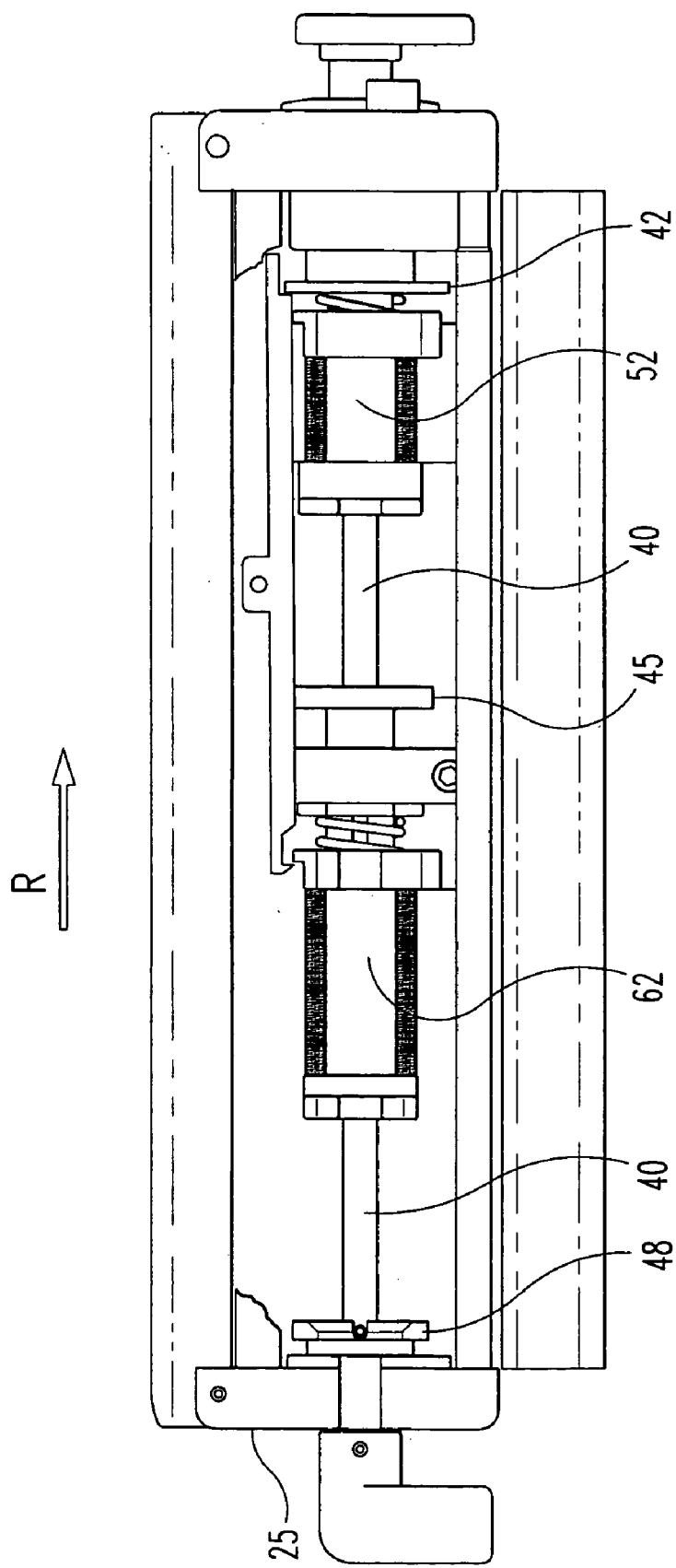

The device 10 shown in FIG. 13 is now ready to fire. Once the device is fired, it returns to the configuration shown in FIG. 8.

Therefore, upon actuation of the cocking lever 70, the forward end 91 of the slider 90 tips toward the forward carrier 62 when the forward carrier 62 is in the resting position, and alternately, the forward end 91 rests upon the forward carrier 62 and the rearward end 96 tips towards the rearward carrier 52 to align the rearward engagement member 97 with the rearward carrier 52 when the forward carrier 62 is in the cocked position.

Figure 20:
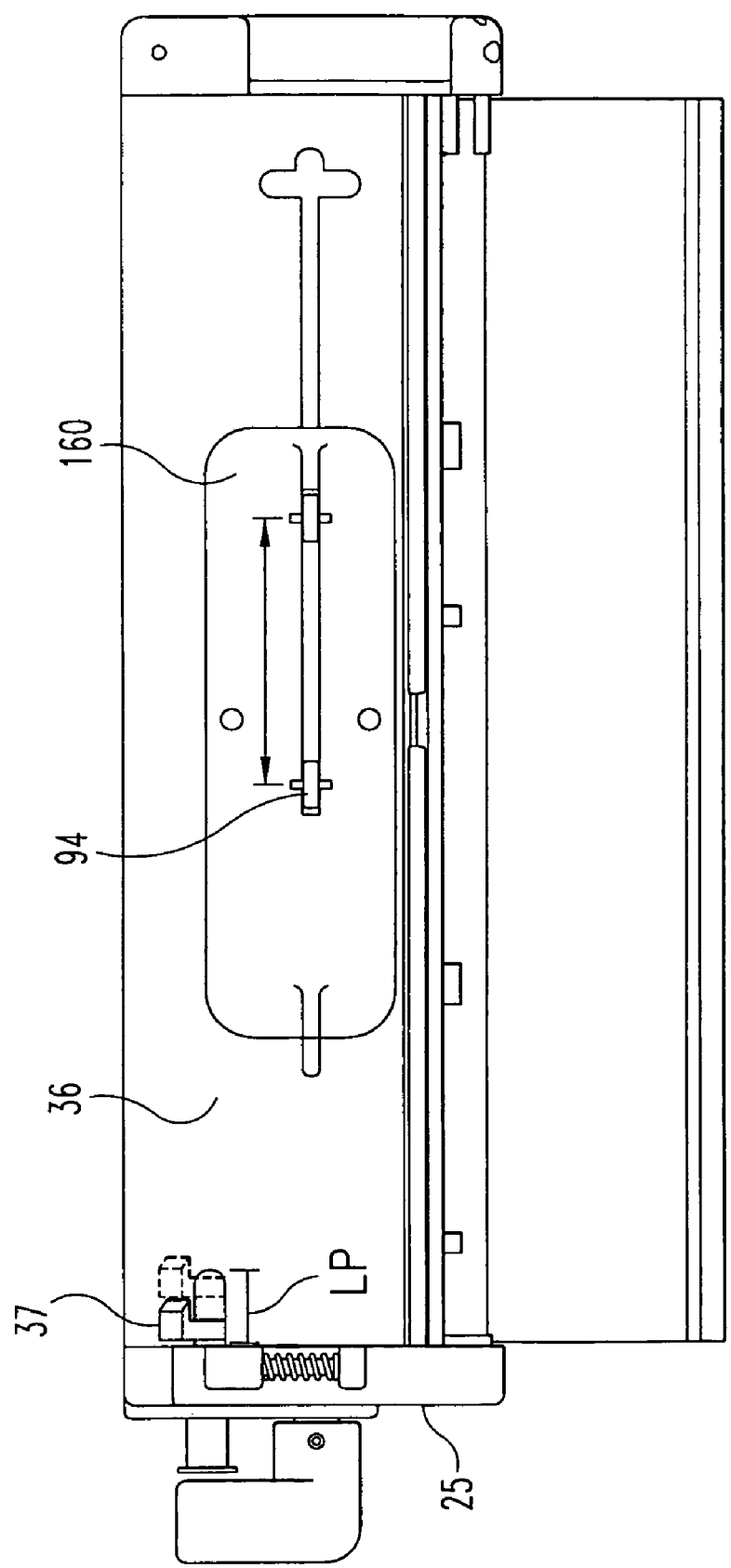
FIG. 20 is a side elevational view of device according to one embodiment of this invention showing details of the lever wall of the housing.

Details of the cocking lever are shown in FIGS. 1, 12 and 17–19. In this specific embodiment, the cocking lever 70 defines a recess 73 for receiving the force transmission mechanism 75 and a groove 72 running parallel to the longitudinal axis l of the housing 20. The groove 72 receives the beam bearing 85 in sliding engagement. A lever hook 74 is disposed on the cocking lever 70 for engaging a lever latch 37, which projects from the lever wall 36. Referring now to FIG. 20, the lever latch 37 is movable along a lever latch path LP between an engaged position adjacent the forward end 25 and a released position towards the rearward end 30.

In this particular embodiment, the latch mechanism includes a safety cam 48 rotatable in response to rotation of one of the safety knobs 130, 140. The safety cam 48 has a major dimension Ds sufficient to block movement of the lever latch 37 along the latch path LP from the engaged position to the released position.

Figure 5:
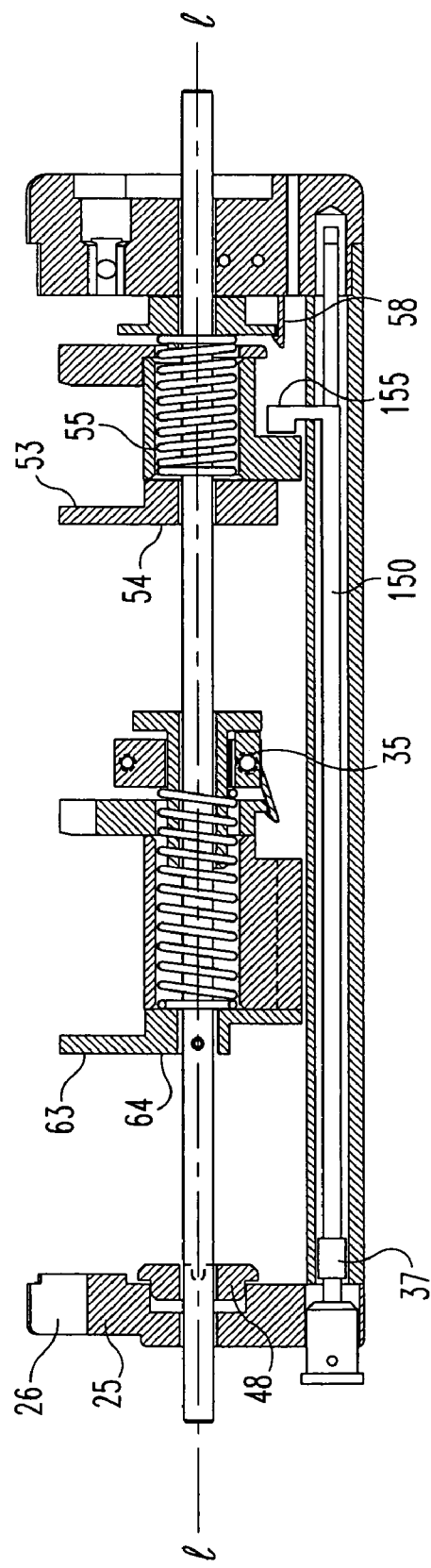
FIG. 5 is a longitudinal section of the view shown in FIG. 3.
Figure 21:
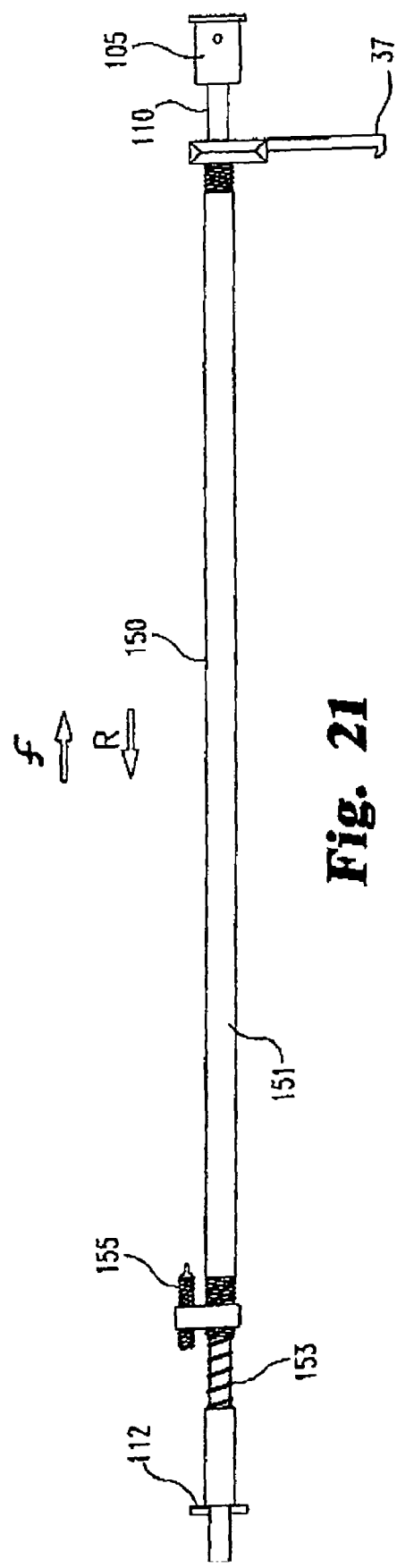
FIG. 21 is a side elevational view of the latch linker and the trigger linker mechanisms of one embodiment of this invention.
Figure 22:
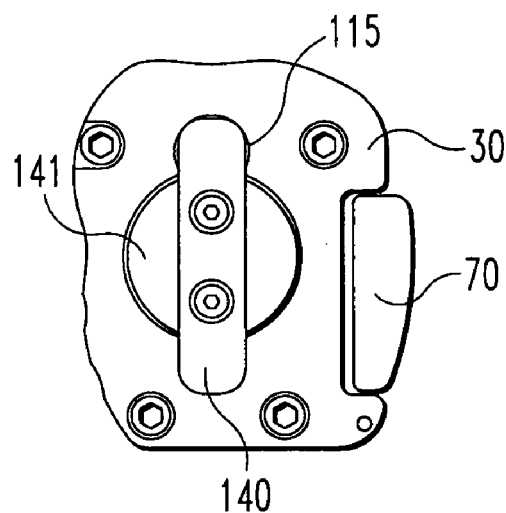
FIG. 22 is an elevational view of the rearward end of a gun according to one embodiment with the safety in the on position.
Figure 23:
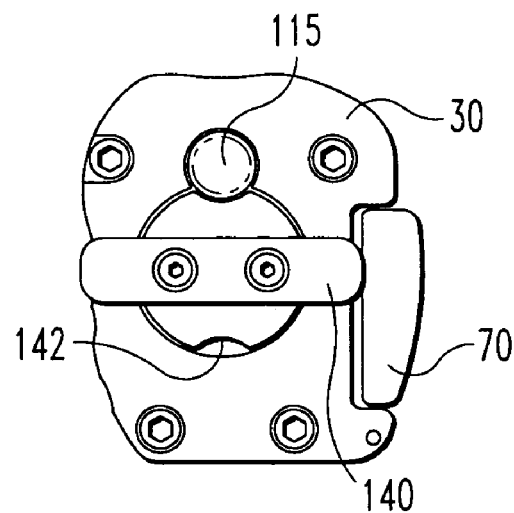
FIG. 23 is an elevational view of the rearward end of the gun shown in FIG. 22 with the safety in the off position.
Figure 24:
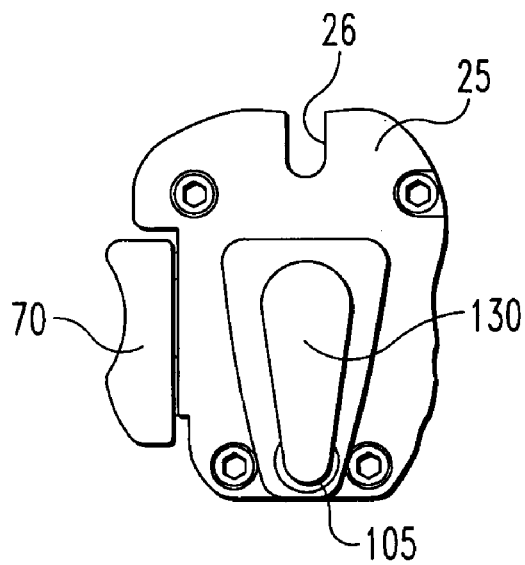
FIG. 24 is an elevational view of the forward end of the gun shown in FIG. 22 with the safety in the on position.
Figure 25:
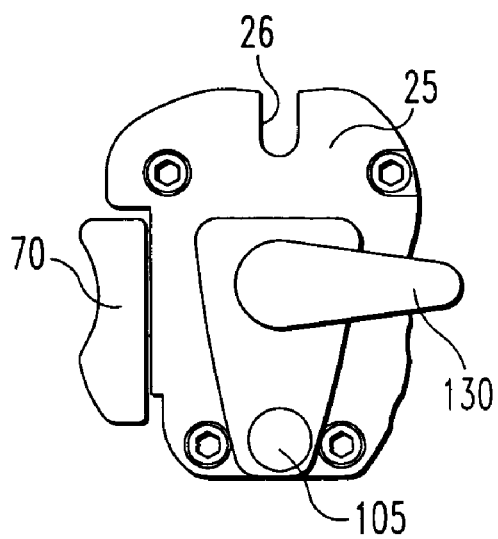
FIG. 25 is an elevational view of the forward end of the gun shown in FIG. 22 with the safety in the off position.

Referring also now to FIGS. 4, 5 and 21, some embodiments provide an elongated lever latch linker 150 positioned parallel to the longitudinal axis l. The lever latch linker 150 operably connects the lever latch 37 to a lever latch pusher 155 disposed in the rearward portion 27 of the housing. In one specific embodiment, the linker 150 includes a hollow tube 151. The lever latch linker 150 is preferably biased in the forward direction along arrow F so that the lever latch is biased in the forward direction f to disengage the lever hook 74. The linker 150 is movable in the rearward direction R in response to movement of the rearward carrier 52 to the first cocked position. When the rearward carrier 52 is in the cocked position, the lever latch pusher 155 is pushed in the rearward direction, which holds the latch 37 in the engaged position. Therefore, when the rearward carrier 52 is in the cocked position, the lever latch 37 is engaged to the lever hook 74 and the cocking lever 70 is closed against the lever wall 36.

Figure 26:
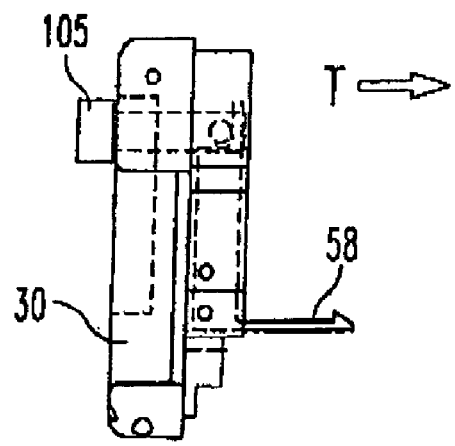
FIG. 26 is a side elevational view of the rearward end of the device of FIG. 22.
Figure 27:
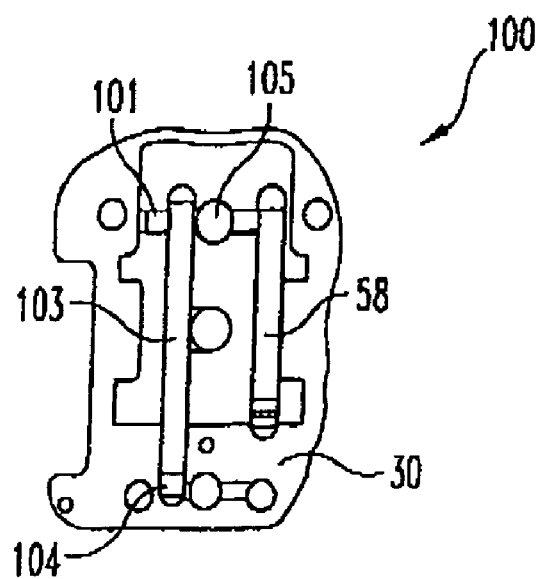
FIG. 27 is an elevational view of the inside of the rearward end of the device of FIG. 22.

In one embodiment, the gun 10 has a front trigger button 105 and a rear trigger button 115. Both of the trigger buttons 105, 115 are operably engaged to the trigger mechanism 100 shown in FIG. 26. The trigger mechanism 100 includes trigger link bar 101 connected to the rearward retaining member 58 and a trigger actuator translator 103, which actuates the trigger mechanism when a force is applied to trigger actuator element 104. When the trigger link bar is pushed in the direction of arrow T, the rearward retaining member 58 is tilted and releases the rearward carrier 52.

Referring again to FIG. 21 the front trigger button 105 is operably linked to the rear trigger button 115 by an elongated trigger link 110. The trigger link 110 is a solid rod, which is coaxially disposed within the lever latch link 150 in one specific embodiment. Pressing the front trigger button 105 causes the trigger link actuator 112 of the trigger link 110 to press the trigger actuator element 104 of the trigger mechanism 100.

The trigger mechanism is automatically blocked by rotating one of the safety knobs 130, 140 to release the cocking lever 70 as discussed above. The safety knobs may physically block access to the trigger buttons, although this is not necessary. In one embodiment, the safety knob 140 includes a flattened skirt member 141 that slides under trigger button 115 to prevent depression of the button. The trigger can be actuated when the safety knob is rotated so that the recess 142 is aligned with the trigger button 115.

Figure 28:
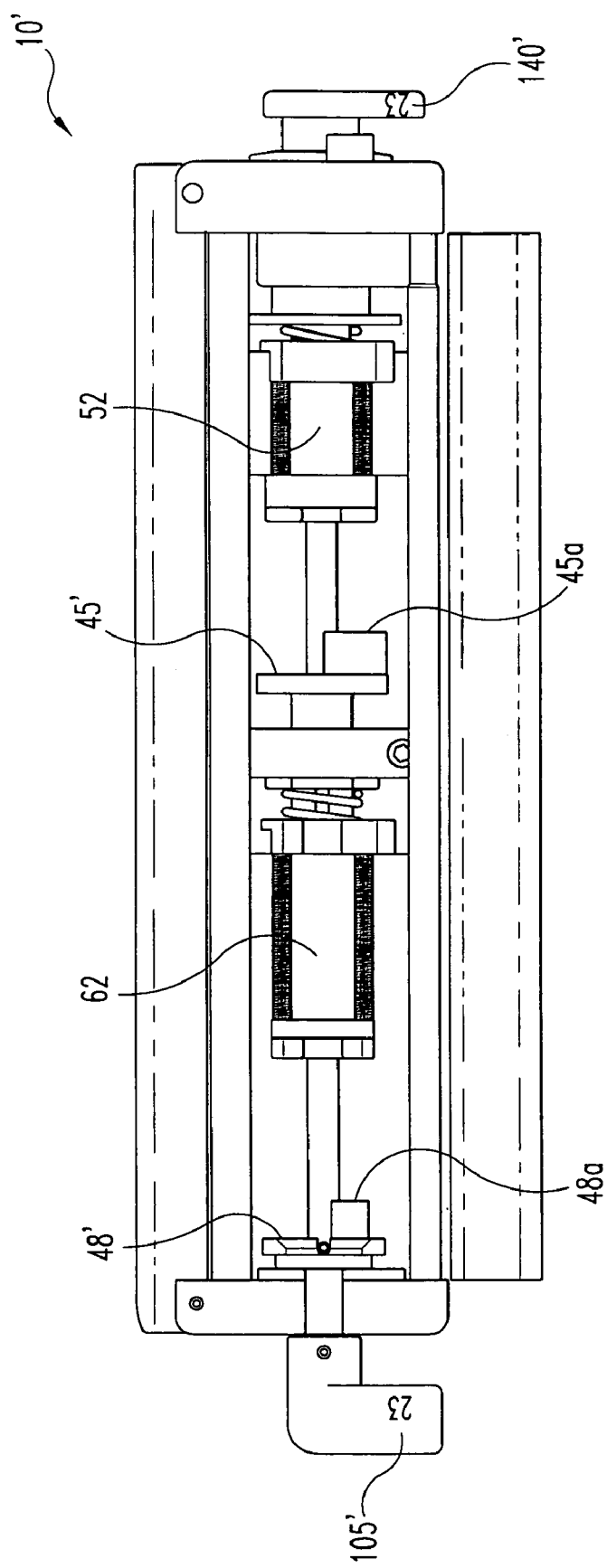
FIG. 28 is a side elevational view of another embodiment of the present invention.
Figure 29:
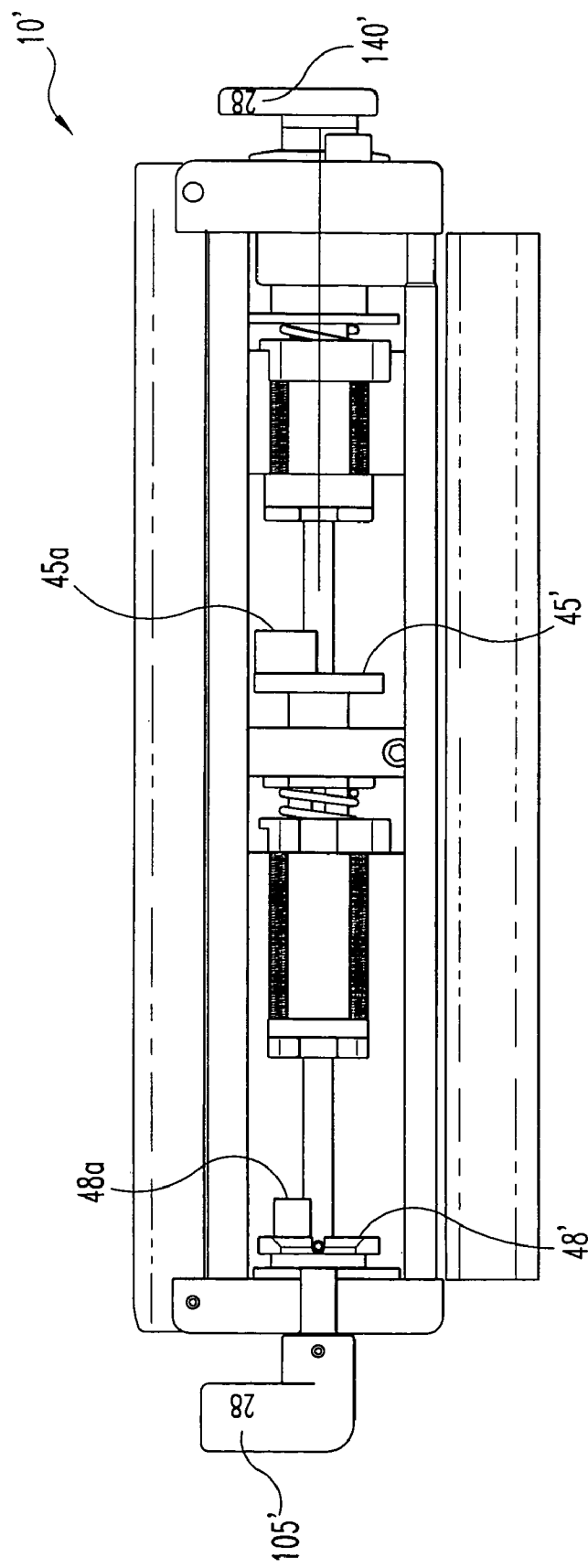
FIG. 29 is a side elevational view of the device shown in FIG. 28 showing the device in another configuration.

In a certain embodiment depicted in FIGS. 28 and 29, the device 10' provides for variable stroke length of the needle set. The alternate stroke lengths are selected by turning one of the safety selector knobs 105', 140'. The safety cam 48' and the center elliptical stop 45' are each provided with a protrusion 45a, 48a that limit the travel of the carriers 62, 52, respectively when a shorter stroke length is selected. For the longer stroke length configuration, the carriers 62, 52 simply pass over the protrusions 45a, 48a.

Figure 30:
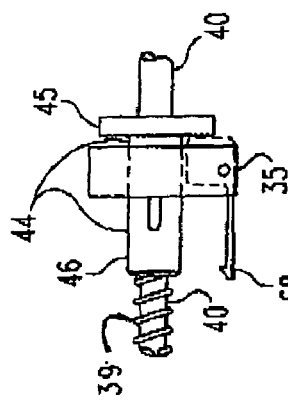
FIG. 30 is a partial view of the center elliptical member according to one embodiment of this invention.
Figure 31:
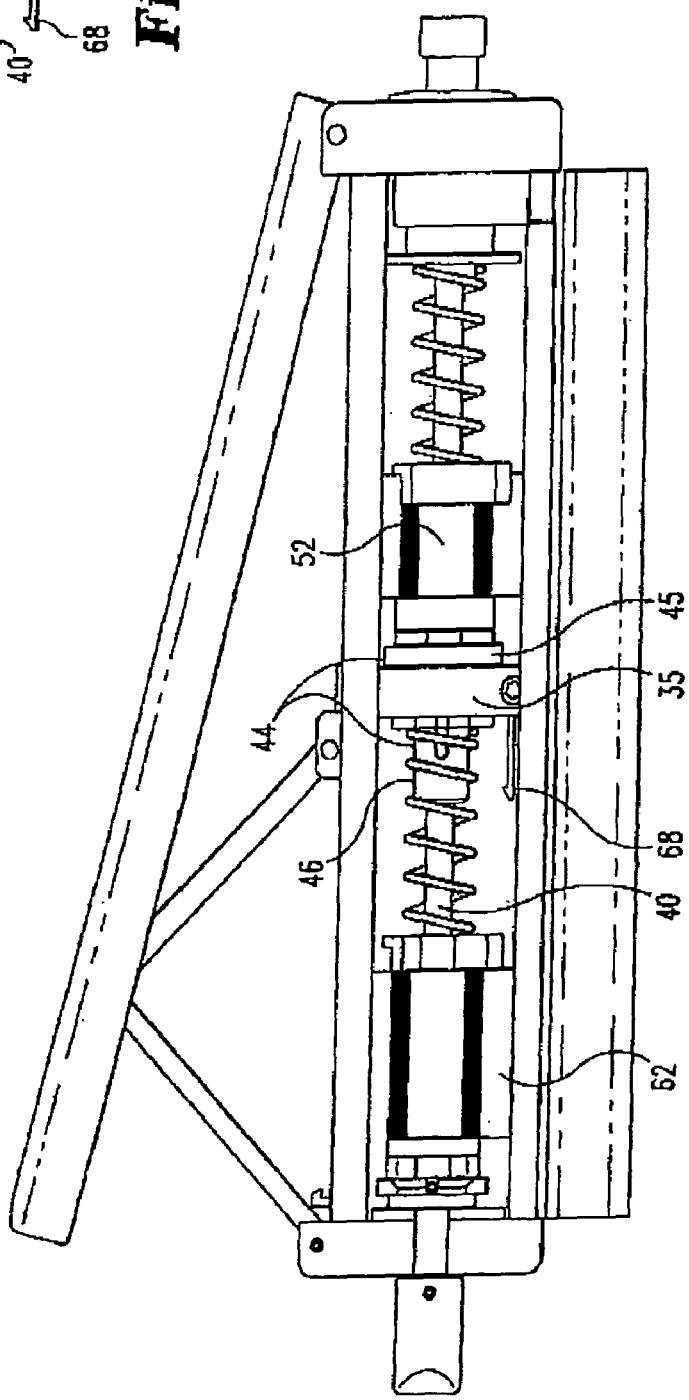
FIG. 31 is a side elevational view of the embodiment shown in FIG. 30.
Figure 32:
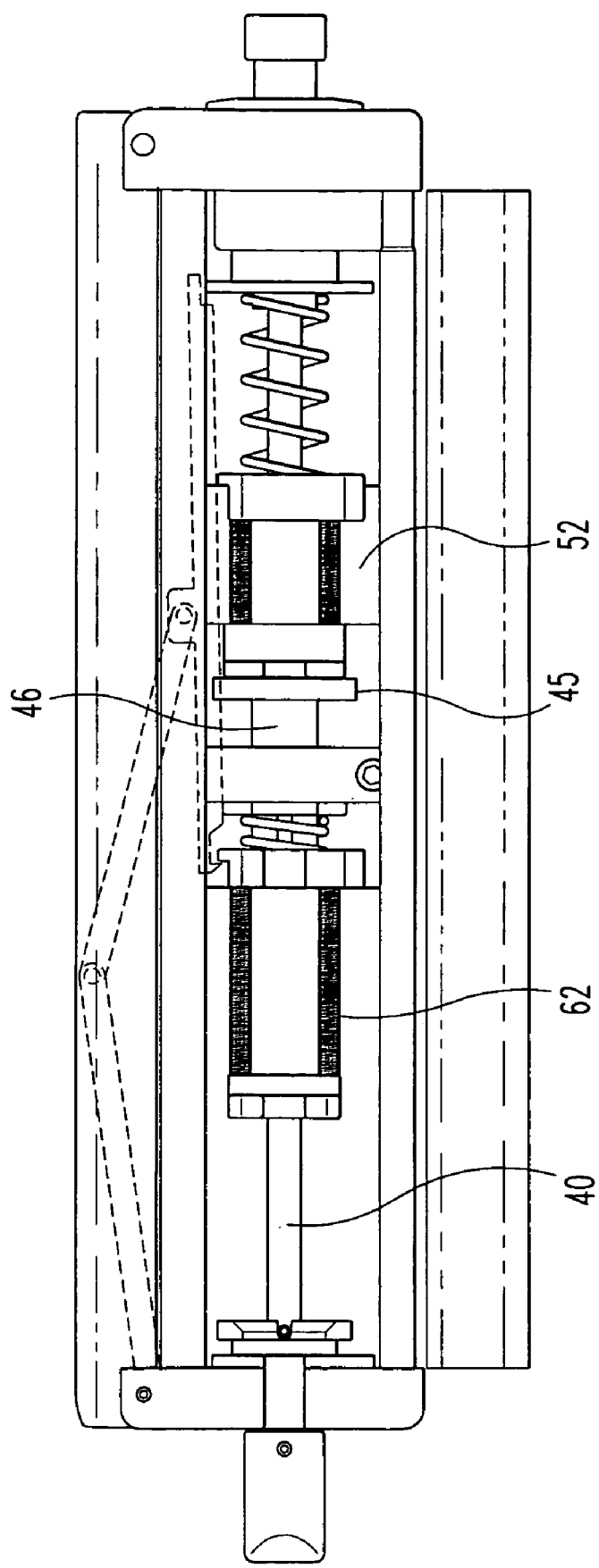
FIG. 32 is a side elevational view of the embodiment shown in FIG. 30.

In one embodiment shown in FIGS. 30–32, the forward retaining member 68 is disposed on the transverse wall 35. The center elliptical member 44 includes the center elliptical plate 45 and a tubular portion 46 coaxially aligned with the center shaft 40. The tubular portion 46 has a diameter greater than an outer diameter of the shaft 40. An internal spring 39 is disposed around the center shaft 40 as shown in FIG. 30 and acts between the tubular portion 46 and the forward carrier 62. The rearward carrier 52 is disposed against the center plate 45 when the rearward carrier 52 is in the resting position as shown in FIG. 31. When the forward carrier 62 is moved to the cocked position shown in FIG. 32, the internal spring 39 pushes the center elliptical member 44, which then acts upon the rear carrier 52 and pushes it to a staging position shown in FIG. 32. The rear carrier 52 is now optimally positioned to receive the rearward engagement member 97 of the cocking slider 90.

In another specific embodiment, a timing plate 160 is provided as shown in FIG. 20. The timing plate 160 helps maintain the slider 90 in proper position.

The sequence of events from the user's perspective is as follows. The user simply loads a needle set into the device 10 as is known in the art. The user then turns one of the safety knobs 130, 140 to cover the respective trigger button 105, 115. The other safety knob turns in unison. The cocking lever 70 is then unlocked and will spring outwardly upon application of slight pressure on the free end 71 of the cocking lever 70. The user cocks the gun by squeezing the cocking lever 70 so that it fully contacts the housing 20 of the device 10. The cocking lever 70 will again spring open, and the gun 10 can be fully cocked by squeezing the cocking lever 70 against the housing 20 of the gun 10. As the cocking lever 70 contacts the housing 20 of the gun 10 a second time, it will be latched and remain closed. The user than simply turns one of the safety knobs 130, 140 to expose the trigger buttons 105, 115, and depresses one of the trigger buttons 105, 115, and the gun fires.

In operation, the device 10 is at first in a resting state wherein the safety knobs 130, 140 are in an open position with the trigger buttons 105, 115 exposed, and the cocking lever 70 is latched in a closed position. When the safety knobs 130, 140 are open, the major axis of the front lever safety cam is perpendicular to the path of the lever latch. The major dimension of the front lever safety cam has a length sufficient to block passage of the lever latch along its path. Since the lever latch cannot move along its path, it cannot disengage the cocking lever hook. In this position, the rocker assembly is disposed within the recess of the cocking lever with the cocking beams extended against the bias of the cocking assembly spring.

When one safety is rotated to obstruct the corresponding trigger, the center shaft, the cams and the opposite safety knob are rotated. In one embodiment, the rear safety blocks movement of the rear trigger, which in turn prevents movement of the front trigger through the trigger link. Rotating one of the safety knobs in turn rotates the front lever safety cam to a position wherein the minor axis is perpendicular to the path of the lever latch. The minor dimension has a length that does not permit it to block the lever latch path, and the lever latch is free to move in a forward direction and disengage the cocking lever hook.

When the cocking lever 70 is released, the force transmission assembly operates to allow the cocking lever 70 to swing open a specific distance. As the cocking lever swings 70 open, the beam bearing 85 slides within the groove defined in the cocking lever and the cocking slider connector slides within its groove so that the cocking lever is in the open position. The cocking beams then are in their retracted position and the cocking slider is lined up to engage the cannula carrier. Depressing the cocking lever applies a force to the pivot point between the cocking beams. This force is transmitted along the inboard beam to depress the connector and the cocking slider so that the cocking slide hook captures a portion of the cannula carrier. Further depressing the cocking lever forces the cocking beams to the extended position. As the slider moves, it pulls the cannula carrier to the cocked position adjacent the center support where it is caught by the cannula carrier catch. As the line of action of the applied force changes (as the beams pivot), a linear force is applied to push the slider forward Since the cocking lever is biased to the open position, the cocking lever then swings open a second time. As the cocking lever swings open, the slider assembly pulls the cocking slider back to its starting position and disengage the cannula carrier. With the cannula carrier in its cocked position, a portion of the carrier bears against the slider causing it to pivot slightly so that the cocking slider is positioned with its pushing surface aligned with a surface of the stylet carrier. As the cocking lever is depressed, the connector pushes against the cocking slider causing it to translate until it engages the stylet carrier. Further pressure on the cocking lever forces the cocking beams to the extended position, which pushes the stylet carrier to the cocked position where it is caught by the stylet carrier catch.

When the stylet carrier travels to the cocked position, it contacts the cocking lever latch pusher, which is operatively connected to the lever latch through the lever latch link tube. The lever latch is moved to engage the locking lever hook, which holds the cocking lever in the closed position.

One of the safety knobs is then rotated to expose the triggers. This in turn rotates the opposite safety knob and the safety cams. The center and rear safety cams rotate so that the major axis intersects the cocking slider. The center and rear cams have a major dimension and a position such that they contact the cocking slider to push it towards the recess in the cocking lever so that both the cannula carriage and the stylet carriage are fully disengaged. The front lever safety cam is also rotated so that the major axis intersects the path of the lever latch. This locks the cocking lever in the closed position.

Depressing one of the triggers moves the stylet carrier catch to release the stylet carrier. The stylet carrier contacts the cannula carrier catch to release the cannula carrier. The two triggers are operatively connected by a trigger link shaft.

Other embodiments of the invention will be apparent to those skilled in the art from consideration of the specification and practice of the invention disclosed herein. It is intended that the specification, drawings and examples be considered as exemplary only, with the true scope and spirit of the invention being indicated by the following claims. It should be understood that only the preferred embodiments have been shown and described and that all changes and modifications that come within the spirit of the invention are desired to be protected.

What is claimed is:

1. An automatic tissue sampling apparatus for use with a biopsy needle set of the kind including an inner needle having a first hub disposed at one end and a cutting point disposed on an opposite end with a tissue holding notch positioned between the cutting point and the first hub and an outer cannula having a second hub at one end and a cutting point disposed at the opposite end, the automatic tissue sampling apparatus comprising:
    a housing having a forward portion adjacent a forward end and a rearward portion adjacent a rearward end with a transverse wall disposed between said forward portion and said rearward portion;
    a rotatable center shaft disposed within said housing along a longitudinal axis of said housing;
    a rearward carrier assembly configured to receive and carry one of the needle hubs, said rearward carrier assembly including
        rearward carrier mounted on said center shaft in said rearward portion and movable along a path substantially parallel to said longitudinal axis of said housing between a first resting position and a first cocked position;
        a rear spring member positioned within said rearward portion of said housing and biasing said rearward carrier forwardly toward said first resting position; and
        a rearward retaining member configured to releasably retain said rearward carrier in the first cocked position, said rearward retaining member releasable in response to a trigger operatively engaged to said rearward retaining member;
    a forward carrier assembly configured to receive and carry the other of the needle hubs, said forward carrier assembly including
        a forward carrier mounted on said center shaft within said forward portion and movable along a path substantially parallel to a longitudinal axis of said housing between a second resting position and a second cocked position;
        a front spring member positioned within said forward portion of said housing and biasing said forward carrier forwardly toward said second resting position; and
        a forward retaining member configured to releasably retain said forward carrier in the second cocked position, said forward retaining member releasable in response to said rearward carrier moving from the first cocked position to the first resting position; and
    a two stage cocking assembly for moving one of said carriers to the corresponding cocked position with a first actuation of said cocking assembly and then moving the other of said carriers to the corresponding cocked position with a second actuation of said cocking assembly, the cocking assembly having
        a cocking lever disposed externally on a lever wall of said housing;
        a force transmission assembly including a forward cocking beam having an opposite end and a first end pivotally attached to said forward end of said housing, a rearward cocking beam having a first end and an opposite end, and a beam bearing engaged to said opposite ends of said forward cocking beam and said rearward cocking beam, each of said cocking beams forming an angle with said lever wall of said housing, said beam bearing movable against said cocking lever between a lever open position with the cocking beams in a retracted position and a lever closed position with the cocking beams in an extended position wherein said angle is smaller when said cocking beams are in the extended position relative to when said cocking beams are in the retracted position;
        a cocking slider having a forward end, a rearward end, a center portion, and a beam-cocking slider connector forward of said center portion, said beam-cocking slider connector pivotally engaged to said first end of said rearward beam and movable along a path in response to actuation of said cocking lever, said cocking slider having a length sufficient to span a distance between said forward carrier and said rearward carrier, said cocking slider disposed between said cocking beams and said carriers to transmit force from said beams to said carriers to move said carriers from the corresponding resting position to the corresponding cocked position,
        said cocking slider having a forward engagement member releasably engageable to said forward carrier and a rearward engagement member releasably engageable to said rearward carrier,
        wherein upon actuation of said cocking lever, said forward end of said cocking slider tips toward said forward carrier to align said forward engagement member with said forward carrier when said forward carrier is in said second resting position, and alternately, said forward end of said cocking slider rests upon said forward carrier and said rearward end of said cocking slider tips towards said rearward carrier to align said rearward engagement member with said rearward carrier when said forward carrier is in said second cocked position.

2. The automatic tissue sampling apparatus of claim 1, wherein said lever wall is disposed between said forward end and said rearward end of said housing and said cocking lever is laterally supported from said lever wall.

3. The automatic tissue sampling apparatus of claim 1, further comprising a trigger operatively engaged to said rearward retaining member and disposed on one of said forward end and said rearward end of said housing, and a safety knob positioned outside one of said forward end and said rearward end of said housing, said safety knob positionable to a safety-on position to block operation of said trigger.

4. The automatic tissue sampling apparatus of claim 3 further comprising a lever hook disposed on said cocking lever, a lever latch engageable to said lever hook and extending from said lever wall, said lever latch movable between an engaged position and a released position, and a safety cam movable in response to movement of said safety knob, said safety cam having a major dimension sufficient to block movement of said lever latch from the engaged position to the released position.

5. The automatic tissue sampling apparatus of claim 4 further comprising an elongated lever latch linker positioned parallel to said longitudinal axis and connecting said lever latch to a lever latch pusher disposed in said rearward portion of said housing, said lever latch pusher biased in the forward direction and movable in a rearward direction in response to movement of said rearward carrier to the first cocked position.

6. The automatic tissue sampling apparatus of claim 4 wherein said safety cam is fixed to said center shaft and said safety knob is operable to rotate said center shaft and said safety cam.

7. The automatic tissue sampling apparatus of claim 6 wherein said safety knob includes a skirt member disposable between said trigger and said one of said forward end and said rearward end to prevent operation of said trigger when said safety knob is in the safety-on position.

8. The automatic tissue sampling apparatus of claim 3 further comprising a second trigger disposed on the other of said forward end and said rearward end of said housing, said trigger and said second trigger operably connected by an elongated trigger linker.

9. The automatic tissue sampling apparatus of claim 3 further comprising a stop member fixed to said center shaft, said stop member having a projection facing one of said forward carrier and said rearward carrier and providing an alternate resting position to the one of said forward carrier and said rearward carrier, said alternate resting position selectable by rotating said safety knob.

10. The automatic tissue sampling apparatus of claim 3 further comprising an elliptical member fixed to said center shaft, said elliptical member having a minor dimension configured to allow said cocking slider to contact said forward carrier and said rearward carrier and a major dimension configured to push said cocking slider away from said forward carrier and said rearward carrier, said major dimension of said elliptical member contacting said cocking slider when said safety knob is in a safety-off position.

11. The automatic tissue sampling apparatus of claim 1, wherein said forward engagement member defines a hook for engaging said forward carrier to pull said forward carrier as said cocking slider slides rearward.

12. The automatic tissue sampling apparatus of claim 11, wherein said rearward engagement member defines a notch for engaging said rearward carrier to push said rearward carrier as said cocking slider slides rearward.

13. The automatic tissue sampling apparatus of claim 1, wherein said rearward engagement member defines a notch for engaging said rearward carrier to push said rearward carrier as said cocking slider slides rearward.

* * * * *